US011820798B2

United States Patent
Carlin et al.

(10) Patent No.: US 11,820,798 B2
(45) Date of Patent: *Nov. 21, 2023

(54) METHOD FOR INCREASING ETEC CS6 ANTIGEN PRESENTATION ON CELL SURFACE AND PRODUCTS OBTAINABLE THEREOF

(71) Applicant: Scandinavian Biopharma Holding AB, Solna (SE)

(72) Inventors: Nils Carlin, Bromma (SE); Ann-Mari Svennerholm, Västra Frölunda (SE); Joshua Tobias, Gothenburg (SE)

(73) Assignee: SCANDINAVIAN BIOPHARMA HOLDING AB, Solina (SE)

( * ) Notice: Subject to any disclaimer, the term of this patent is extended or adjusted under 35 U.S.C. 154(b) by 412 days.

This patent is subject to a terminal disclaimer.

(21) Appl. No.: 17/104,456

(22) Filed: Nov. 25, 2020

(65) Prior Publication Data

US 2021/0147491 A1    May 20, 2021

Related U.S. Application Data (60) Continuation of application No. 16/567,190, filed on Sep. 11, 2019, now Pat. No. 10,851,140, which is a continuation of application No. 15/726,957, filed on Oct. 6, 2017, now Pat. No. 10,414,806, which is a continuation of application No. 15/009,645, filed on Jan. 28, 2016, now Pat. No. 9,790,257, which is a division of application No. 14/239,732, filed as application No. PCT/EP2012/067598 on Sep. 10, 2012, now Pat. No. 9,273,103.

(60) Provisional application No. 61/533,405, filed on Sep. 12, 2011.

(30) Foreign Application Priority Data

Sep. 12, 2011  (SE) .................................... 1150821-5

(51) Int. Cl.
| | |
|---|---|
| *C07K 14/245* | (2006.01) |
| *A61K 39/108* | (2006.01) |
| *A61K 39/00* | (2006.01) |
| *G01N 33/569* | (2006.01) |
| *C12N 15/70* | (2006.01) |
| *A61K 38/00* | (2006.01) |

(52) U.S. Cl.
CPC .... *C07K 14/245* (2013.01); *A61K 39/001102* (2018.08); *A61K 39/0258* (2013.01); *A61K 38/00* (2013.01); *A61K 39/0011* (2013.01); *A61K 2039/521* (2013.01); *A61K 2039/545* (2013.01); *A61K 2039/575* (2013.01); *C12N 15/70* (2013.01); *G01N 33/56916* (2013.01); *Y02A 50/30* (2018.01)

(58) Field of Classification Search
CPC .......................... C07K 14/245; A61K 39/0258
See application file for complete search history.

(56) References Cited

U.S. PATENT DOCUMENTS

| | | | |
|---|---|---|---|
| 9,273,103 B2* | 3/2016 | Carlin | ...................... A61P 31/04 |
| 9,790,257 B2* | 10/2017 | Carlin | ................ A61K 39/0258 |
| 10,414,806 B2* | 9/2019 | Carlin | ................ A61K 39/0258 |
| 10,851,140 B2* | 12/2020 | Carlin | ................ A61K 39/0258 |
| 2002/0034522 A1 | 3/2002 | Adlam et al. | |
| 2004/0005662 A1 | 1/2004 | Cassels et al. | |
| 2009/0081166 A1 | 3/2009 | Lebens et al. | |

FOREIGN PATENT DOCUMENTS

| | | |
|---|---|---|
| CN | 101378780 A | 3/2009 |
| EP | 1444987 A2 | 8/2004 |
| JP | H11-512746 A | 11/1999 |
| JP | 2005-504002 A | 2/2005 |
| JP | 2010-180228 A | 8/2010 |
| RU | 2242993 | 12/2004 |
| WO | WO 92/14487 A1 | 9/1992 |
| WO | WO 00/37106 | 6/2000 |
| WO | WO 03/022306 | 3/2003 |
| WO | WO 03/076643 A2 | 9/2003 |
| WO | WO 2007089205 | 8/2007 |

OTHER PUBLICATIONS

Russian Office Action and English Translation in Russian Application No. 2014114284/10(022340), filed Sep. 10, 2012, dated Aug. 24, 2016.

Tobias, Joshua et al., "Over-expression of major colonization factors of enterotoxigenic *Escherichia coli*, alone or together, on non-toxigenic *E. coli* bacteria" Vaccine, Oct. 8, 2010, pp. 6977-6984, vol. 28, No. 43.

(Continued)

*Primary Examiner* — Brian Gangle
*Assistant Examiner* — Lakia J Jackson-Tongue
(74) *Attorney, Agent, or Firm* — KNOBBE, MARTENS, OLSON & BEAR LLP (57) ABSTRACT

A method for increase the presentation of ETEC CS6 antigen on a cell surface, comprising the step of contacting cells expressing said antigen with an aqueous solution comprising 0.6-2.2 percent phenol by weight, such that the presentation of said antigen is increased by at least 100%. A method for the manufacture of a killed whole cell vaccine for immunization against CS6-expressing ETEC. Cells and vaccines obtainable by the above methods.

22 Claims, 5 Drawing Sheets
Specification includes a Sequence Listing.

(56) References Cited

OTHER PUBLICATIONS

Tobias, Joshua et al., "Construction of a non-toxigenic *Escherichia coli* oral vaccine strain expressing large amounts of CS6 and inducing strong intestinal and serum anti-CS6 antibody responses in mice" Vaccine, Nov. 2011, pp. 8863-8869, vol. 29, No. 48.
International Search Report for PCT/EP2012/067598 dated dated Nov. 19, 2012.
Chinese Office Action dated Jan. 30, 2015 in Chinese Application No. 201280043926.8, filed Sep. 10, 2012.
Japanese Office Action, dated May 25, 2016, received in corresponding Japanese Patent Application No. 2014-529010.

* cited by examiner

METHOD FOR INCREASING ETEC CS6 ANTIGEN PRESENTATION ON CELL SURFACE AND PRODUCTS OBTAINABLE THEREOF

CROSS-REFERENCE TO RELATED APPLICATIONS

This application is a continuation of U.S. patent application Ser. No. 16/567,190, filed on Sep. 11, 2019, which is a continuation of U.S. patent application Ser. No. 15/726,957, filed on Oct. 6, 2017, which issued as U.S. Pat. No. 10,414,806 on Sep. 17, 2019, which is a continuation of U.S. patent application Ser. No. 15/009,645, filed on Jan. 28, 2016, which issued as U.S. Pat. No. 9,790,257 on Oct. 17, 2017, which is a divisional of U.S. patent application Ser. No. 14/239,732, filed on Feb. 19, 2014, which issued as U.S. Pat. No. 9,273,103 on Mar. 1, 2016, which is the U.S. National Phase Application of PCT International Application Number PCT/EP2012/067598, filed on Sep. 10, 2012, designating the United States of America and published in the English language, which is an International Application of and claims the benefit of priority to Swedish Patent Application No. 1150821-5, filed on Sep. 12, 2011, and U.S. Provisional Application No. 61/533,405, filed on Sep. 12, 2011. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-NOV001-001C3.txt, the date of creation of the ASCII text file is Nov. 24, 2020, and the size of the ASCII text file is 1.2 KB.

FIELD

The present invention relates to methods useful in the preparation of ETEC CS6 antigen, in particular for the manufacture of vaccines, as well as cells and vaccines obtainable through the method.

BACKGROUND

*Coli* surface antigen 6 (CS6) is one of the most prevalent non-fimbrial colonization factors (CFs) of enterotoxigenic *Escherichia coli* (ETEC) bacteria, which are the most common cause of diarrhea among infants and children in developing countries and in travelers to such areas.

Since immune protection against ETEC is mainly mediated by locally produced IgA antibodies in the gut, much effort is focused on the development of an oral CF-based vaccine. ETEC candidate vaccines inducing anti-CF immune responses have been developed, e.g. in the form of a combined CF-ETEC+CTB oral vaccine that contained five killed ETEC strains expressing several of the most commonly encountered CFs, i.e. CFA/I, CS1, CS2, CS3, CS4, and CS5, together with recombinant cholera toxin B subunit (CTB, which is highly homologous to the B subunit of ETEC LT) (Levine M M, Giron J A, Noriega F. Fimbrial vaccines. In: P. Klemm editor. Fimbriae: adhesion, biogenics, genetics and vaccines, CRC Press, Boca Raton, Fla.1994, p. 255-70; Svennerholm A-M, Tobias J. Vaccines against enterotoxigenic *Escherichia coli*. Expert Rev Vaccines 2008; 7:795-804).

Previous work has described the preparation of candidate *E. coli* vaccine strains expressing immunogenic amounts of fimbrial CF antigens such as CFA/I and CS2, which are retained after formalin treatment. However, attempts to generate *E. coli* expressing immunogenic amounts of CS6 and to preserve the immunological activity of the CS6 protein in a killed whole-cell vaccine have failed until now. Here is described the construction of a recombinant non-toxigenic *E. coli* strain, with a non-antibiotic selection marker thyA, which expresses large amounts of CS6 antigen on the bacterial surface, and show that phenol inactivation of the bacteria does not destroy the CS6 antigen properties. To the contrary, it was unexpectedly found that phenol treatment significantly increased the amount of antigen presented on the cell surface. This increase is very relevant, since the number of cells that can be included in an oral whole cell vaccine is a major limiting factor in vaccine development, due to the fact that too large numbers of bacteria given orally give rise to adverse effects such as vomiting, especially in infant subjects. By increasing the amount of antigen presented per cell, the amount of antigen(s) can be increased in the vaccine without increasing the overall number of cells in the vaccine.

Oral immunization of mice with such phenol-killed CS6 over-expressing *E. coli* bacteria induced strong fecal and intestinal IgA and serum IgG+IgM antibody responses to CS6 that exceeded the responses induced by an ETEC reference strain naturally expressing CS6 and previously used as a vaccine strain. The data indicate that the described phenol-inactivated non-toxigenic and CS6 over-expressing *E. coli* strain is a useful component in an oral ETEC vaccine.

DEFINITIONS

In the context of the present disclosure, the terms below have the following meanings.

The abbreviation ETEC refers to enterotoxigenic *Escherichia coli* bacteria.

The term CS6 antigen means *Coli* surface antigen 6, one of the most prevalent non-fimbrial colonization factors of ETEC bacteria. The term ETEC CS6 antigen is used synonymously.

The term killed whole cell vaccine refers to vaccine containing whole (intact) but killed (non-living) bacteria.

The term non-antibiotic selection marker refers to genetic selection markers for selection of plasmids not requiring the use of antibiotics in the selection process. Examples include thyA (thymidylate synthase) complementation.

SUMMARY

In a first aspect, there is disclosed a method for increasing the presentation of ETEC CS6 antigen on cell surface, comprising the step of contacting cells expressing said antigen with an aqueous solution comprising 0.6-2.2 percent phenol by weight, such that the presentation of said antigen is increased by at least 100%, preferably at least 200%, more preferably at least 300%.

Preferably, the duration of the contacting step is 1 to 72 h. More preferably, the duration of the contacting step is 1.5 to 42 h.

Preferably, the temperature during the contacting step is 18 to 42° C., more preferably 18 to 38° C., even more preferably 18-22° C. or 36-38° C.

Preferably, the phenol concentration is 0.8-2.0 percent by weight, more preferably 1.0-2.0 percent by weight.

Preferably, the cells comprise *Escherichia coli* cells. Preferably, the antigen is recombinantly overexpressed by the cells.

Preferably, the method of the first aspect further comprises the step of comparing the presentation of the antigen by the cells to the presentation of CS6-antigen by untreated but otherwise comparable cells by means of an inhibition ELISA or dot blot, preferably inhibition ELISA.

In a second aspect, there is also disclosed a method for the manufacture of a killed whole cell vaccine for immunization against CS6-expressing ETEC, comprising the method according to any of the preceding claims, wherein the phenol concentration, the contacting temperature and the contacting time are chosen such that at least 107-fold inactivation of the cells occurs concomitantly with the increase in CS6 antigen presentation.

Preferably, in the method of the second aspect, the phenol concentration is 0.6-2.0 percent by weight, the contacting time is 6-72 h and the contacting temperature is 18-22° C. More preferably, the phenol concentration is 0.75-0.85 percent by weight, the contacting time is 40±2 h and the contacting temperature is 20±1° C.

In a third aspect, there is disclosed a cell obtainable by the method according to the first or the second aspects.

In a fourth aspect, there is disclosed a vaccine for immunization against CS6-expressing ETEC, comprising cells of the third aspect.

DETAILED DESCRIPTION

Method for Increasing Presentation of CS6-Antigen

In a first aspect, the present invention provides a method for increasing the presentation of ETEC CS6 antigen on a cell surface, characterized by that it comprises the step of contacting a cell or cells expressing said antigen with an aqueous solution comprising 0.6-2.2 percent phenol by weight, at a suitable temperature and for a suitable time, such that the presentation of said antigen is increased by at least 20%. By the at least 20% increase in antigen presentation is meant that the amount of antigen present of the cell surface and detectable by suitable methods (see below for details) is at least doubled compared to cells not having been subjected to the method but which are otherwise comparable. Preferably, the increase in antigen presentation is at least 30%, 40%, 50%, 60%, 70%, 80% or 90%, more preferably at least 100%, 125%, 150%, 175%, 200%, 250% or 300%. Most preferably, the increase is at least 100%.

The aqueous solution may e.g. be phosphate buffered saline (PBS) with added phenol, but many different aqueous buffers are suitable. It is preferable that the pH of the buffers is 5-9, more preferably 6-8, most preferably 6.5 to 7.5. The salt concentration of the buffer is preferably 50-200 mM, more preferably 100-150 mM and most preferably about 137 mM. A suitable PBS buffer can be as follows: 8 g NaCl, 0.2 g KCl, 1.44 g $Na_2HPO_4$, 0.24 g $KH_2PO_4$, in 1 liter, pH 7.4.

The variables phenol concentration, temperature and time exhibit a certain degree of interdependency. If the temperature is increased, lower phenol concentration and/or shorter time is required to achieve the increased presentation (and vice versa). If the treatment time is lengthened, lower phenol concentration and/or lower temperature can be utilized (and vice versa). Aided by the guidance from the teachings herein, the skilled person will be able to use routine experimentation without significant burden to adapt the combination of phenol concentration, time and temperature to the needs at hand.

Suitable duration for the treatment may be 0.1 to 240 h or 1 to 240 h. Preferably, the treatment time may be 1 to 72 h. More preferably, the treatment time may be 1.5 to 42.0 h. Most preferably, the treatment time is 2.0-40.0 h.

Suitable temperature for the treatment is in the range of 1-45° C. or 4-45° C. Preferably, the temperature may be 18 to 42° C. From practical point of view, it may be preferable to perform the method at ambient (room) temperature to avoid the need for specialized equipment to maintain the temperature. Thus one preferred temperature range is 18-25° C., even more preferably 18-22° C., most preferably about 20° C. It may also be preferable to perform the method at an elevated temperature to shorten the process duration and/or to reduce the required phenol concentration. Thus another preferred temperature range is 35-42° C., even more preferably 36-38° C., most preferably about 37° C.

The phenol concentration may preferably be in the range of 0.7 to 2.0 percent by weight, more preferably 0.75-2.0 percent by weight, yet more preferably 0.8-2.0 percent by weight, still more preferably 0.85-2.0 percent by weight, even more preferably 0.9-2.0 percent by weight, and most preferably 1.0-2.0 percent by weight. In one preferred embodiment, the phenol concentration is 0.6-2.0 percent by weight, the contacting time is 6-72 h and the contacting temperature is 18-22° C. In another preferred embodiment, the phenol concentration is 0.6-2.0 percent by weight, the contacting time is 2-4 h and the contacting temperature is 36-38° C.

The cells in the above method may be *Escherichia coli* cells. This may be advantageous from practical point of view since *E. coli* is readily grown and genetically manipulated in the laboratory. Furthermore, the principal purpose of the method is to provide vaccines against ETEC, whereby it may be advantageous to use an *E. coli* host for the antigen to provide a more natural context for the antigen being presented. Preferably, the cells are non-toxigenic *E. coli* cells. Nevertheless, it should be understood the method can be used with other CS6-expressing cells as well.

The cell concentration is not crucial within reasonable limits. Any concentration up to $10^{12}$ cells/ml is considered feasible. A practical preferable cell concentration range may be $10^8$-$10^{12}$ cells/ml. The most preferable range is $10^9$ to $2 \cdot 10^{10}$ cells/ml.

The ETEC CS6 antigen production may be recombinantly induced in the cell, by way of genetic engineering (see Example 1). This facilitates the production of high levels of the antigen per cell, advantageous for minimizing the number of cells needed for a vaccine dose, leading to minimized adverse effects. Nevertheless, the method can also be used with cells that natively (i.e. without any genetic engineering) express the CS6 antigen. Preferably however, the cells of the method are non-toxigenic *E. coli* host cells that overexpress CS6-antigen as a result of transformation with a CS6-expressing plasmid. Preferably, the plasmid has a non-antibiotic selection marker, i.e. a selection marker that does not require the use of antibiotics for its function. Most preferably, the host cells are auxotrophic for thymidine and the CS6-overexpressing plasmid carriers a thymidylate synthase (ThyA) complementating factor, whereby the selection can be carried out using a medium devoid of thymidine. Preferably the CS6-overexpression is driven by a tac-promoter or a similar strong inducible promoter well known in the art.

In terms of measuring the increased presentation of the CS6 antigen as a result of the method of the invention, useful methods are disclosed herein and are also known from the literature. Preferably, the determination is performed using an inhibition ELISA assay as disclosed herein (see Example 2 and the associated Materials and Methods), or by means of a dot blot also disclosed herein (see Example 2). Preferably, the method of the first aspect comprises the further steps of analyzing the amount of presentation of the CS6-antigen by the cells (e.g. using the above techniques) and comparing the amount presented to the amount of CS6-antigen presented by cells which were not subjected to the treatment with aqueous solution comprising phenol but which are otherwise comparable. Suitably, a portion of cells is taken aside and stored before the contacting step to serve as such a control sample.

Method for Manufacture of a Vaccine

In a second aspect, the present disclosure provides a method for the manufacture of a killed whole cell vaccine for immunization against CS6-expressing ETEC, comprising the method according to the first aspect, wherein the phenol concentration, contacting temperature and contacting time are chosen such that at least $10^7$-fold inactivation of the cells occurs concomitantly with the increase in CS6 antigen presentation. Preferably, the degree of inactivation is at least $10^8$-fold, more preferably $10^9$-fold, yet more preferably $10^{10}$-fold and most preferably there are no viable cells present after the treatment. Cell inactivation can be determined by any common means well known in the art. A suitable method is disclosed herein in the section titled Materials and Methods.

The utilization of phenol for cell inactivation as well as increasing antigen presentation may be advantageous since this reduces the number of process steps in vaccine manufacture. The phenol inactivation also solves the problem resulting from the propensity of the CS6-antigen being destroyed the normally preferable inactivation method, formalin treatment (see Example 2).

Preferably, in the method of the second aspect, the phenol concentration is 0.6-2.0 percent by weight, the contacting time is 6-72 h and the contacting temperature is 18-22° C. Alternative preferred set of conditions is where the phenol concentration is 0.6-2.0 percent by weight, the contacting time is 2-4 h and the contacting temperature is 36-38° C. Yet another preferred set of conditions is where the phenol concentration is 1.1-1.3 percent by weight, the contacting time is 16±3 h and the contacting temperature is 20±2° C. Still another preferred set of conditions is where the phenol concentration is 1.1-1.3 percent by weight, the contacting time is 40±8 h and the contacting temperature is 20±2° C. Further preferred set of conditions is where the phenol concentration is 1.4-1.6 percent by weight, the contacting time is 6±2 h and the contacting temperature is 20±2° C. Yet further preferred set of conditions is where the phenol concentration is 0.75-0.85 percent by weight, the contacting time is 40±2 h and the contacting temperature is 20±1° C.

Cells and Vaccines Obtainable Through the Method of the Invention

In a third aspect, a cell obtainable by the method according the first or second aspects is provided. The phenol treatment results in an apparent change in the structure of the cell wall and/or the antigen such that more of the antigen is more available for detection (both in vitro e.g. by antibodies and in vivo by the immune system). In other words, the bacterial cell thus treated has acquired a novel structure by way of the method of the first or second aspects, although it is not feasible to describe the change in structure in structural terms.

In a fourth aspect there is provided a vaccine for immunization against CS6-expressing ETEC, comprising cells according to the third aspect.

EXAMPLES

For details on the experimental procedures relating to the examples, the reader is referred to the section titled Materials and Methods.

Example 1: Expression of CS6 in *E. coli* C600-CS6

Figure 1A:
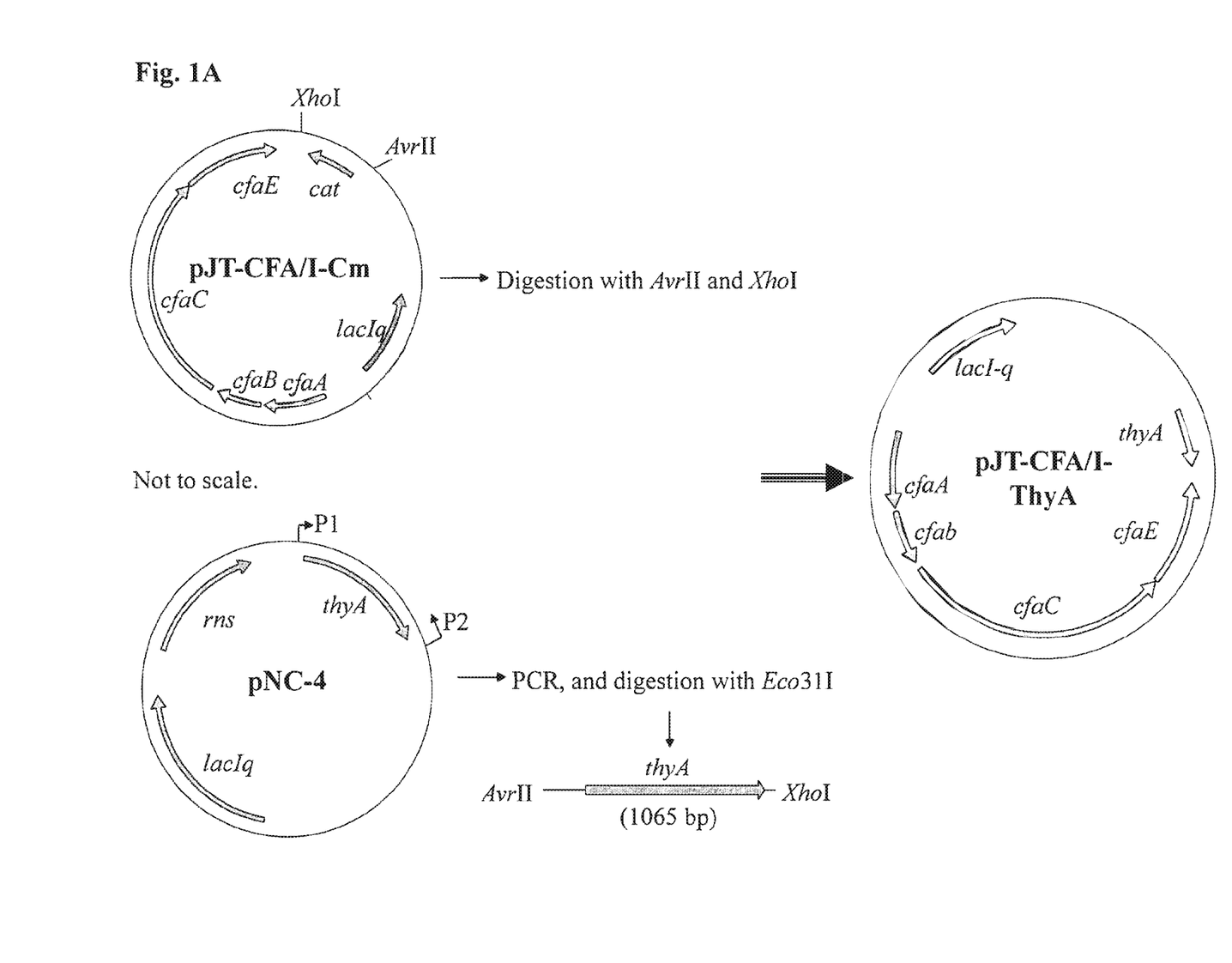
FIGS. 1A and 1B: Construction of pJT-CS6-thyA for expression of CS6. The plasmid pJT-CFA/I-ThyA was first constructed (FIG. 1A), and then the CFA/I operon was replaced with the entire amplified CS6 operon creating pJT-CS6-thyA (FIG. 1B).
Figure 1B:
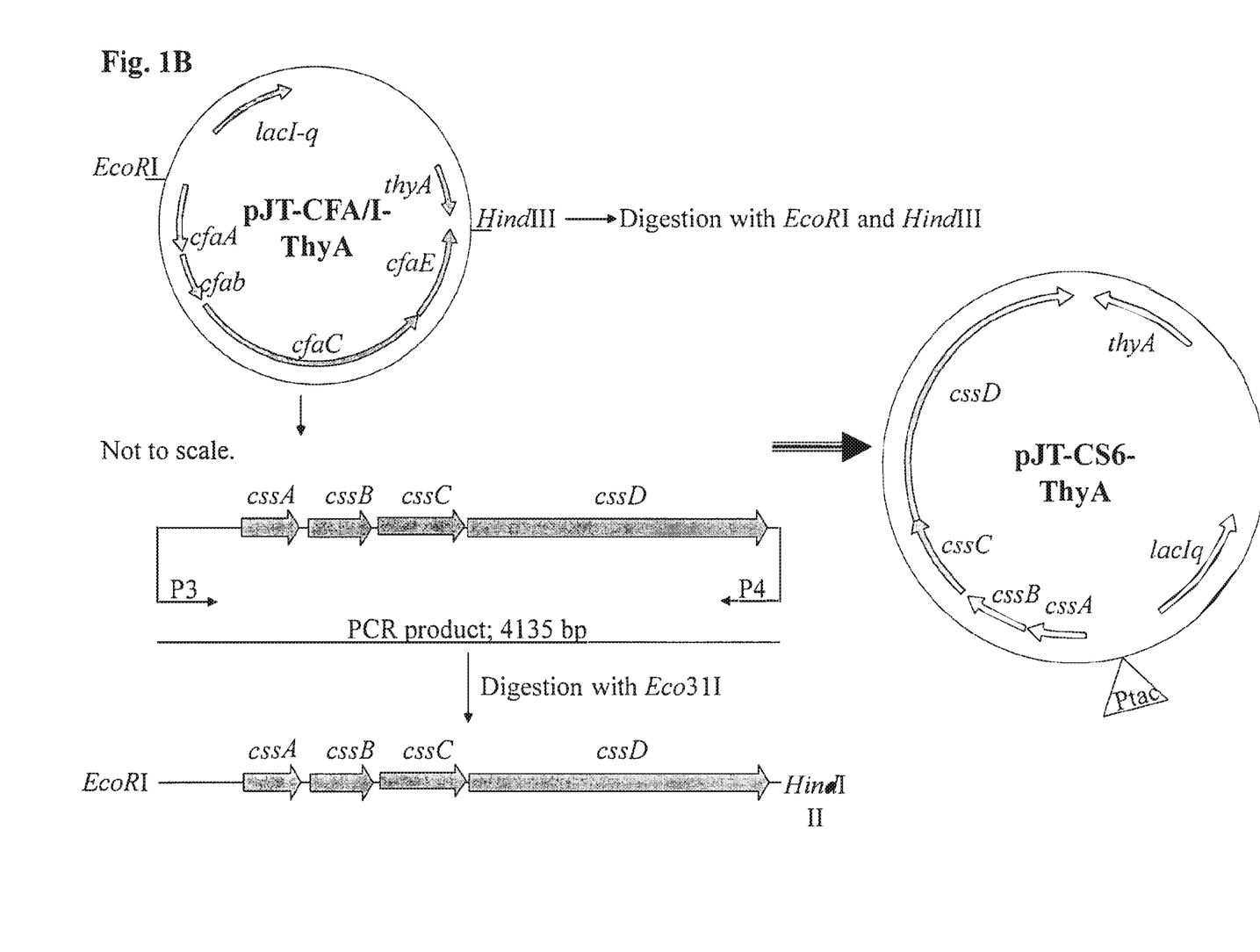
Figure 2A:
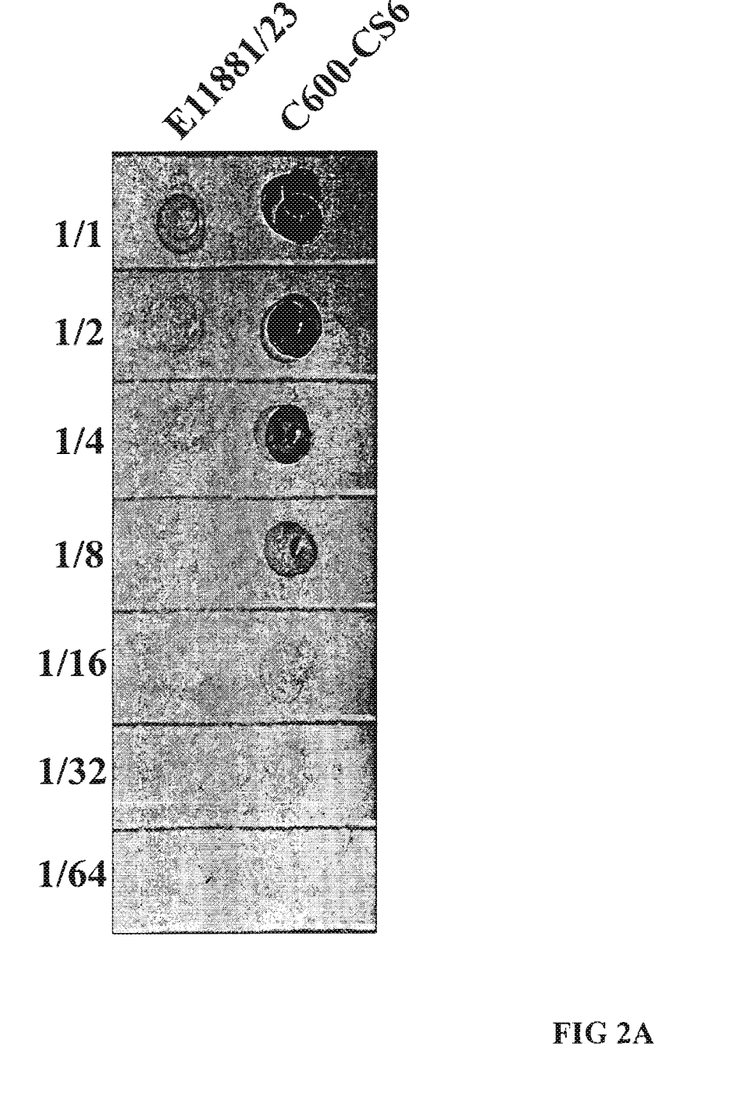
FIGS. 2A and 2B: Surface expression of CS6 on the C600-CS6 recombinant strain and the CS6 reference strain E11881/23 examined by dot blot (FIG. 2A) and inhibition ELISA (FIG. 2B). Both strains were cultured in liquid CFA medium, the recombinant strain induced with IPTG, both washed and tested in serial dilutions at an initial density of 109 bacteria/ml. **$P<0.01$ by Student's t test, two-tailed.
Figure 2B:
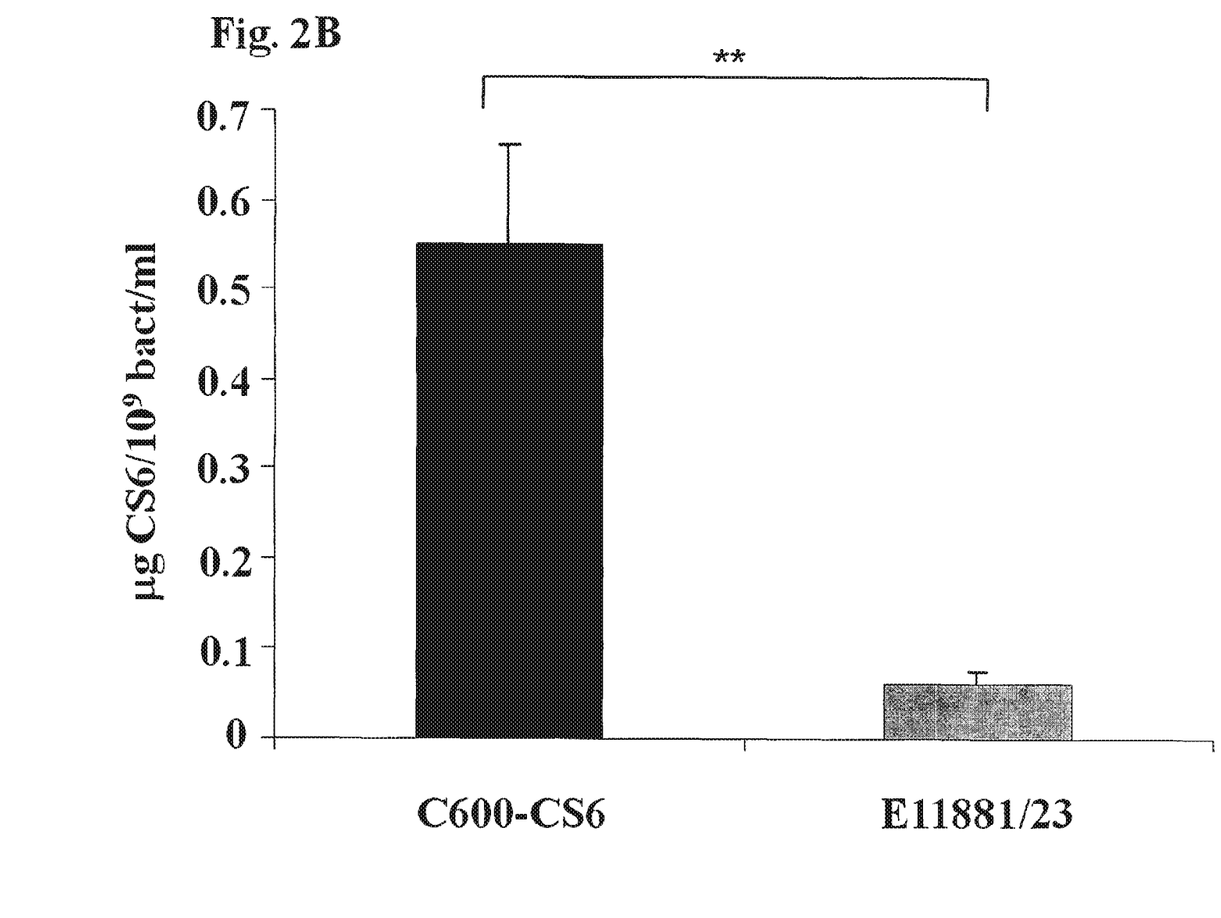

A DNA fragment carrying the structural genes (cssA, cssB, cssC, cssD) for CS6, prepared from a wild-type ETEC strain with surface expression of CS6, was amplified by PCR and cloned to construct the expression vector pJT-CS6-ThyA, as depicted in FIGS. 1A and 1B. This plasmid was then electroporated into the thymine dependent, non-toxigenic *E. coli* C600-ΔthyA strain, and CS6 surface expression was induced by addition of IPTG to the growth medium, as shown in an immuno-dot blot assay (FIG. 2A). No CS6 expression was observed in the absence of the inducer (data not shown). When examining the expression of CS6 by the recombinant C600-CS6 strain using the dot blot assay, we found that this strain expressed at least 8-fold higher levels of CS6 compared to the CS6 reference strain E11881/23, which had previously been used as CS4+CS6 vaccine strain in the CF-CTB-ETEC vaccine (FIG. 2A). Likewise, also when specifically determining the surface expression of CS6 using an inhibition ELISA assay, an approximately 10-fold larger amount of CS6 was found on the recombinant strain as compared with the reference strain (FIG. 2B).

EXAMPLE 2: INACTIVATION OF BACTERIA WITHOUT DESTROYING THE CS6 ANTIGEN PROPERTIES

With the aim to kill the CS6 expressing bacteria while preserving the CS6 antigen properties on their surface, the effects of formaldehyde and phenol were compared. Preliminary studies showed that treating the bacteria with 0.3% or 0.6% formaldehyde, while safely killing the bacteria, resulted in a complete loss of detectable CS6 antigen (data not shown). In contrast, treating the bacteria with 0.5% phenol not only killed the tested bacteria, but also preserved the CS6 antigen (data not shown); a lower tested concentration of phenol, 0.25%, on the other hand did not result in complete killing of the bacteria. These results indicated that phenol treatment could be useful for inactivating the bacteria while preserving the CS6 antigen. To work out an optimal inactivation method, different concentrations of phenol were therefore tested for inactivation of both the recombinant C600-CS6 strain and for comparison another CS6 over-expressing strain (TOP10-CS6-Amp). As seen in Table 2, with both strains tested with 0.5%, 0.8%, 1%, and 1.6%, but not with 0.25%, of phenol inactivated the bacteria and also preserved the surface CS6, as tested by inhibition ELISA. The maximal level of CS6 was found when the bacteria were inactivated with 0.8% phenol, which treatment did in fact reproducibly increase the estimated amounts of CS6 antigen surface compared to the untreated bacteria (Table 2). Based on these results, phenol at the concentration of 0.8% was therefore used to inactivate both C600-CS6 and the reference strain E11881/23, which resulted in killed bacteria with 6-fold larger amounts of CS6 on the recombinant strain than on the reference strain, as tested by inhibition ELISA. These inactivated bacteria were then used for oral immunizations of mice.

TABLE 2

Surface CS6 levels and lack of growth of C600-CS6 and TOP10-CS6-Amp strains, after inactivation with difference concentrations of phenol.

| Phenol | CS6 ($\mu$g/$10^9$ bacteria)[a] | | Growth[b] | |
| --- | --- | --- | --- | --- |
| | C600-CS6 | TOP10-CS6-Amp | C600-CS6 | TOP10-CS6-Amp |
| 0 | 0.61 ± 0.038 | 0.39 ± 0.054 | + | + |
| 0.25% | 0.55 ± 0.037 | 0.30 ± 0.06 | + | + |
| 0.5% | 0.53 ± 0.046 | 0.77 ± 0.084 | − | − |
| 0.8% | 2.03 ± 0.23 | 2.36 ± 0.206 | − | − |
| 1.0% | 1.92 ± 0.18 | 1.87 ± 0.13 | − | − |
| 1.6% | 1.15 ± 0.11 | 0.89 ± 0.082 | − | − |

[a]Levels of surface CS6 were measured by inhibition ELISA as described in materials and methods; values mean ± SE of four determinations.
[b]Following inactivation with phenol, the treated bacteria were tested for sterility (i.e. lack of growth) as described in materials and methods; − indicates no growth, and + indicates growth.

Example 3: Immunogenicity of Phenol-Killed C600-CS6 in Mice

Figure 3:
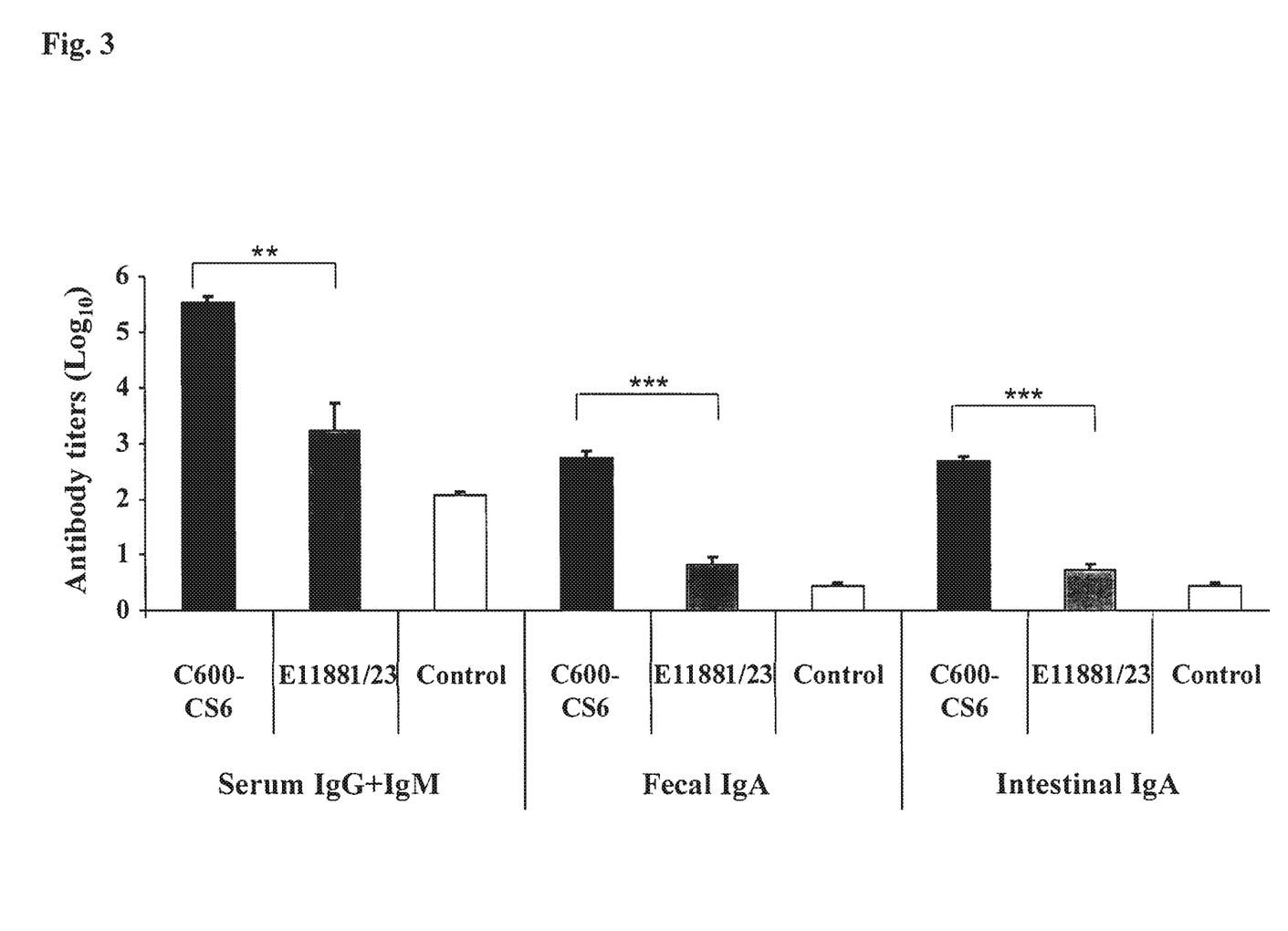
FIG. 3: Serum IgG+IgM, and fecal- and intestinal-extract ELISA IgA titers against CS6, after oral immunization of C57 Bl/6 mice with the same numbers of phenol-killed C600-CS6 bacteria and E11881/23 bacteria (n=5 mice/group). Titers are shown as geometric mean (GM)+standard error (SE) for the mice in each group; for fecal and intestinal extracts the levels are adjusted to the total IgA levels in the extracts. Controls refer to antibody levels in mice before immunization. P<0.01, *P<0.001, by Student's t test, two-tailed.

In a first test of the immunogenicity of the recombinant strain C600-CS6 we immunized groups of both Balb/C and C57 Bl/6 mice with the same number of phenol-killed bacteria, and the serum antibody responses to CS6, as measured by ELISA, were compared. Although significant anti-CS6 responses were induced in both types of mice, the antibody responses in C57 Bl/6 mice were substantially higher than in the Balb/C mice (data not shown). We therefore used C57 Bl/6 mice for the further oral immunization studies in which the immunogenicity of orally administered phenol-killed vaccine preparation of C600-CS6 and the reference strain E11881/23 were compared. The results showed that all immunized mice responded with production of serum IgG+IgM antibodies against CS6, and that the titers of antibodies against CS6 on average were more than 60-fold higher in mice immunized with C600-CS6 bacteria than those in mice immunized with the reference strain E11881/23 (FIG. 3) Fecal and intestinal IgA antibody responses against CS6 were also examined (FIG. 3). In both cases the recombinant C600-CS6 strain induced significantly, on average 75-fold higher levels of fecal and intestinal IgA antibodies against CS6 when compared to the levels in mice immunized with the corresponding reference strain; the latter strain only induced marginally higher mucosal IgA anti-CS6 levels than those seen in unimmunized control mice.

Example 4: Optimization of Phenol Treatment Increasing CS6 Antigen-Presentation at 20° C.

The C600-CS6 strain was cultured for overnight (16-18 h) in a rotary shaker (150 rpm) at 37° C. Aliquots of the overnight culture was diluted 1/100 and the resulting culture incubated for 2 h as above, after which IPTG was added to a final concentration of 1 mM to induce expression of CS6. The culture was then further incubated at the same conditions for an additional 6 h. The bacteria were then harvested, washed twice with PBS (to avoid presence of any residues from the medium), and re-suspended in PBS to a density of OD600=16 (corresponding to approximately $2\times10^{10}$ bacteria/ml).

The induced, OD-adjusted bacterial culture was divided into 8 flasks of 250 ml, each containing 25 ml of the bacterial culture. As time zero (i.e. non-treated bacteria) a portion was taken for viable counting. Twenty five (25) ml of phenol to the final concentration (percent by weight) of 0.2, 0.4, 0.6, 0.8, 1.0, 1.2, 1.5, or 2.0 were added into the flasks, followed by incubation of all the flasks for 1 h, 2 h, 6 h, 16 h, and 40 h, at room temperature with 80 rpm. After each time point, 1 ml of each bacterial suspension (with phenol) was removed from each flask to an Eppendorf tube. The bacteria were harvested, washed thoroughly twice with PBS (to avoid presence of any residues from the phenol), and re-suspended with 1 ml of PBS. The suspensions were stored at 4° C. and used for inhibition ELISA. The results are shown in Table 3.

TABLE 3

Surface CS6 levels on C600-CS6 strain, after inactivation with different concentrations of phenol for different times at 20° C.

| | CS6 ($\mu$g/$10^9$ bacteria)[a] | | | |
| --- | --- | --- | --- | --- |
| | Incubation times | | | |
| Phenol | 0 h | 6 h | 16 h | 40 h |
| 0 | 0.3 | | | |
| 0.6% | | 0.17 | 0.28 | 0.73 |
| 0.8% | | 0.28 | 0.77 | 0.89 |
| 1.0% | | 1.1 | 0.93 | 1.06 |
| 1.2% | | 1.67 | 2.2 | 1.36 |
| 1.5% | | 2.75 | 1.71 | 1.14 |
| 2.0% | | 1.57 | 0.91 | 0.37 |

[a]Levels of surface CS6 were measured by inhibition ELISA as described in materials and methods. Values are the mean of two determinations

Example 5: Phenol Treatment Increasing CS6 Antigen-Presentation and Simultaneously Inactivating Bacteria in Industrial Scale A 500 liter fermentor was inoculated with an *E. coli* strain overexpressing the CS6 antigen (ETEX 24). After induction of expression by IPTG the fermentation was continued for 8 hours. The bacteria were harvested and washed over a 500 kD ultrafilter and finally dispensed at a concentration of $20 \times 10^9$ bacteria/ml. Phenol was added to a final concentration of 0.8% (w/v) and the suspension was kept at 20° C. for 40 hours under constant stirring. The suspension was washed over a 500 kD ultrafiltration membrane in phosphate buffered saline and stored at 4° C.

During the inactivation procedure samples were taken before inactivation after 1, 2, 18 and 40 hours of inactivation to test for viability. Briefly, samples taken were washed by centrifugation and resuspended in the original volume in PBS whereafter dilutions were made in PBS and plated on Colonization Factor Agar (CFA agar). Plates were incubated at 37° C. and counted the following day.

Inhibition ELISA to quantitate the amount of CS6 antigen was done on fresh material before inactivation and washed inactivated material.

It is clearly apparent that efficient cell inactivation and increased CS6 antigen presentation can be achieved simultaneously in industrial production scale (Table 4).

TABLE 4

Time course for inactivation at 20° C.

|  | Inactivation time (h) | | | | |
| --- | --- | --- | --- | --- | --- |
|  | 0 | 1 | 2 | 18 | 40 |
| Total CS6 (µg/$10^9$ cells) | 2.51 | Nd | Nd | Nd | 5.36 |
| Bound CS6 (µg/$10^9$ cells) | 1.01 | Nd | Nd | Nd | 2.90 |
| Viable cells (cfu/ml) | $1.64 \times 10^{10}$ | $1.5 \times 10^5$ | $1.2 \times 10^3$ | 0 | 0 |

Nd = not determined

Materials and Methods

Bacterial Strains and Culture.

The bacterial strains used in this study are listed in Table 1. A non-toxigenic C600-ΔthyA *E. coli* strain, which is auxotrophic to thymine (N. I. A. Carlin and M. Lebens, unpublished) was used for construction of the vaccine candidate strain C600-CS6. The ETEC strain E11881/23, which had previously been used as a CS4+CS6 expressing strain in the CF-ETEC+CTB vaccine, was used as a reference strain. For expression of CS6, bacteria were grown in CFA medium (Evans D G, Evans D J Jr., Clegg S, Pauley J A. Purification and characterization of the CFA/I antigen of enterotoxigenic *Escherichia coli*. Infect Immun 1979; 25:738-48), supplemented with ampicillin (100 µg/ml) when necessary.

TABLE 1

List of strains, plasmids, and primers used in this study

| Strains, plasmid and primers | Relevant characteristic | Reference/source |
| --- | --- | --- |
| Strains: | | |
| ETEC GB35 | CS6+, LT+ | Nicklasson Microb Pathog 2008; 44: 246-54. |
| *E. coli* E11881/23 | CS4+, CS6+, ST- | |
| TOP10-CS6-Amp | TOP10 expressing CS6, Amp$^r$ | Tobias Vaccine 2008; 26: 5373-80 |
| *E. coli* C600-ΔthyA | Auxotrophic to thymine; Kan$^r$ | NIA Carlin and M Lebens |
| C600-CFA/I | C600-ΔthyA/pJT-CFA/I-ThyA | This study |
| C600-/CS6 | C600-ΔthyA/pJT-CS6-ThyA | This study |
| Plasmid: | | |
| pJT-CFA/I-Cm | 9041 bp | Tobias Vaccine 2010; 28: 6977-84. |
| pNC-4 | 5086 bp; thyA | NIA Carlin |
| pJT-CFA/I-thyA | 8879 bp; thyA | This study |
| pJT-CS6-ThyA | 7973 bp; thyA | This study |
| Primers: | | |
| Primers: | | |
| P1 | 5'-CGGTCTCCCTAGGCCTCCTTACCTATGGTGATC (SEQ ID NO: 1) | |
| P2 | 5'-CGGTCTCCTCGAGCGACTCTAGACCTAACCG (SEQ ID NO: 2) | |
| P3 | 5'-CGGTCTCGAATTCTAATGGTGTTATATGAAGAAAACAATTG (SEQ ID NO: 3) | |
| P4 | 5'-CGGTCTCAAGCTTAACATTGTTTATTTACAACAGATAATTGTTTG (SEQ ID NO: 4) | |

Construction of Expression Vector pJT-CS6-ThyA.

For construction of the C600-CS6 recombinant strain, the plasmid pJT-CFA/I-ThyA was first generated. The plasmid pJT-CFA/I-Cm (Tobias J, Holmgren J, Hellman M, Nygren E, Lebens M, Svennerholm A-M. Over-expression of major colonization factors of enterotoxigenic *Escherichia coli*, alone or together, on non-toxigenic *E. coli* bacteria. Vaccine 2010; 28:6977-84) was digested with XhoI and AvrII to remove the chloramphenicol resistance gene (cat). The plasmid pNC-4 (N. I. A. Carlin; unpublished) was then used in a PCR reaction to amplify the thyA gene (from *Vibrio cholerae*). The forward primer P1 (SEQ ID NO: 1) was homologous to a sequence starting 98 bp upstream of thyA and had restriction sites for Eco31I and AvrII, and the reverse primer P2 (SEQ ID NO: 2) was homologous to a sequence ending 75 bp downstream of thyA, and had restriction sites for Eco31I and XhoI, at the 5' end (Table 1). PCR conditions were as follows: 95° C. for 5 min, 31 cycles of 94° C. for 15 s, 58° C. for 30 s and 72° C. for 50 sec, with a final extension of 7 min at 72° C. The resulting 1065 bp fragment containing thyA was then gel-extracted and cleaved with XhoI and AvrII. Ligation of the amplified and digested thyA with the digested pJT-CFA/I-Cm resulted in pJT-CFA/I-ThyA (FIG. 1A). This plasmid was then electroporated into *E. coli* C600-ΔthyA, and a recombinant strain (C600-ΔthyA/pJT-CFA/I-ThyA) was isolated.

The plasmid pJT-CS6-ThyA was then constructed in two steps (FIG. 1B). First, the pJT-CFA/I-ThyA plasmid was digested with EcoRI and HindIII. PCR was used to amplify the CS6 operon from the CS6-expressing ETEC strain GB35 (Nicklasson M, Sjoling A, Lebens M, Tobias J, Janzon A, Brive L, Svennerholm A-M. Mutations in the periplasmic chaperone leading to loss of surface expression of the colonization factor CS6 in enterotoxigenic *Escherichia coli* (ETEC) clinical isolates. Microb Pathog. 2008; 44:246-54). Amplification was carried out using the forward and reverse primers P3 (SEQ ID NO: 3) and P4 (SEQ ID NO: 4), respectively (Table 1) and the Expand High Fidelity PCR System (Roche Diagnostics GmbH). P3 is homologous to a sequence starting 13 bp upstream of cssA and carries restriction sites for EcoRI and Eco31I, whereas P4, which is homologous to a sequence ending 2 bp downstream of the cssD, carries restriction sites for HindIII and Eco31I, at the 5' end (FIG. 1B). PCR conditions were as described previously (Tobias J, Lebens M, Källgård S, Nicklasson M, Svennerholm A-M. Role of different genes in the CS6 operon for surface expression of enterotoxigenic *Escherichia coli* colonization factor CS6. Vaccine 2008; 26:5373-80). The amplified CS6 operon, 4135 bp, was then restricted with Eco31I, resulting in a fragment with flanking EcoRI and HindIII, which was ligated with the digested pJT-CFA/I-ThyA resulting in a 7973 bp pJT-CS6-ThyA plasmid. The constructed plasmid pJT-CS6-ThyA was electroporated into the C600-ΔthyA strain. The resulting colonies were screened for the presence of CS6 operon by PCR using the primers P3 and P4. Positive clones were further analyzed by restriction analysis of isolated plasmids, and also by the ability to grow in CFA medium confirming their thymine independence. One such clone was selected as a CS6 positive and thymine independent strain, and designated C600-CS6 (i.e. C600-ΔthyA/pJT-CS6-ThyA).

Expression of CS6.

The CS6 expressing strains were cultured in CFA medium, overnight (16-18 h) in a rotary shaker (150 rpm) at 37° C. Aliquots of the overnight cultures were diluted 1/100 in CFA medium and the resulting cultures were incubated for 2 h as above. Into the culture of the recombinant strain, IPTG was added to a final concentration of 1 mM to induce expression of CS6, and then cultures were further incubated at the same conditions for an additional 6 h. The bacteria were then harvested and re-suspended in PBS to a density of OD600=0.8 (corresponding to approximately $10^9$ bacteria/ml).

Quantification of CS6 on the Recombinant Strain.

A specific monoclonal antibody (MAb 2a:14) against CS6 (Helander A, Grewal H M, Gaastra W, Svennerholm A-M. Detection and characterization of the *coli* surface antigen 6 of enterotoxigenic *Escherichia coli* strains by using monoclonal antibodies. J Clin Microbiol 1997; 35:867-72) was used to quantify the level of expression of CS6 by the recombinant C600-CS6 and the ETEC reference E11881/23 strains, using dot-blot and inhibition ELISA methods, as described (Tobias J, Holmgren J, Hellman M, Nygren E, Lebens M, Svennerholm A-M. Over-expression of major colonization factors of enterotoxigenic *Escherichia coli*, alone or together, on non-toxigenic *E. coli* bacteria. Vaccine 2010; 28:6977-84 and Tobias J, Lebens M, Bolin I, Wiklund G, Svennerholm A-M. Construction of non-toxic *Escherichia coli* and *Vibrio cholerae* strains expressing high and immunogenic levels of enterotoxigenic *E. coli* colonization factor I fimbriae. Vaccine 2008; 26:743-52.)

Preparation of Inactivated Bacteria.

Formaldehyde and phenol were tested and compared for inactivation of the CS6 expressing strains. Formaldehyde, in final concentrations of 0.3% (w/v; 0.1M) or 0.6% (0.2M), and phenol in final concentrations of 0.25%-1.6% (w/v; 0.026-0.17M), were added to bacterial cultures at a density of $10^{10}$ bacteria/ml in PBS. The suspensions were incubated for 2 h at 37° C. with shaking at 60 rpm, and then kept at 4° C. for 3 days without agitation. The bacterial suspensions were then centrifuged, washed, and re-suspended in the same volume of PBS and kept at 4° C. until use. In both inactivation methods, 0.1 ml of each suspension was spread onto blood agar and incubated at 37° C. for up to one week to check for lack of growth. Before being used for oral immunization, the level of CS6 on the inactivated bacteria was checked by inhibition ELISA.

Mouse Immunizations and Sample Collection.

Groups of female Balb/C and C57 Bl/6 mice (Charles River; 6-8 weeks of age; 5 mice/group) were used for oral (intragastric) immunizations. All mice were given two doses of $3\times10^8$ phenol-killed bacteria (inactivated, using 0.8% concentration of phenol) of either C600-CS6 or the reference strain together with 7.5 µg CT two days apart in 0.3 ml 3% sodium bicarbonate solution intragastrically through a baby feeding catheter (first round of immunization), followed two weeks later by two identical immunizations two days apart in a second round of immunization. Bleedings were performed before the first immunization and two weeks after the last immunization, at which times fecal pellets (FPs) were also collected and extracts prepared as described previously (Nygren E, Holmgren J, Attridge S R. Murine antibody responses following systemic or mucosal immunization with viable or inactivated *Vibrio cholerae*. Vaccine 2008; 26:6784-90). In addition, at the later time point when the mice were sacrificed, they were perfused with a heparin-PBS solution to remove blood from the tissues, and small intestinal tissue collected and extracted with a 2% (w/v) Saponin-PBS solution (the Perfext method) as described previously Villavedra M, Carol H, Hjulstrom M, Holmgren J, Czerkinsky C. "PERFEXT": a direct method for quantitative assessment of cytokine production in vivo at the local level. Res Immunol 1997; 148:257-66).

ELISAs.

IgG+IgM and IgA antibody titers against CS6 were determined in sera, fecal and intestinal extracts, by ELISA, as described previously (Rudin A, Svennerholm A-M. Colonization factor antigens (CFAs) of enterotoxigenic *Escherichia coli* can prime and boost immune responses against heterologous CFAs. Microb Pathog 1994; 16:131-9). CS6, for use as coating antigen (at the final concentration of 0.7 µg/ml) in ELISAs, was purified from the previously described TOP10-CS6 over-expressing strain (Tobias J, Lebens M, Källgård S, Nicklasson M, Svennerholm A-M. Vaccine 2008; 26:5373-80), by sequential ammonium sulphate precipitation and gel filtration. Sera from individual mice were tested using low-binding microtiter plates (Greiner), and samples were initially diluted 1/100 followed by serial three-fold dilutions. Fecal pellet extracts and small intestine tissue extracts were tested in high-binding microtiter plates (Greiner) in 3-fold serial dilutions from a starting dilution of 1/3. Antibody titers were calculated as the reciprocals of the sample dilutions which gave an A450 absorbance of 0.4 above the background value. In the fecal and intestinal extract samples, total IgA was also measured by ELISA as described (Nygren E, Holmgren J, Attridge SR. Vaccine 2008; 26:6784-90), and antigen-specific IgA antibody values were expressed as IgA titer units per µg of total IgA.

Statistical Analysis.

All ELISA experiments were done at least twice on different occasions.

Statistical analyses were conducted by Student's t-test, and $P<0.05$ (two-tailed) was regarded as a significant difference.

---

What is claimed is:

1. A method for the manufacture of a vaccine for immunization against *Coli* surface antigen 6 "CS6"-expressing enterotoxigenic *Escherichia coli* "ETEC", said vaccine comprising a phenol-treated cell having an amount of CS6 antigen presented on a cell surface, the method comprising:
   contacting a cell expressing said antigen with an aqueous solution comprising 0.6-2.0 percent phenol by weight;
   selecting a duration of contacting time from 1 to 72 h; and
   selecting a temperature during the contacting time from 18 to 42° C.;
   wherein the phenol concentration, duration of contacting time, and temperature are chosen such that the presentation of said CS6 antigen is increased by at least 100%, as detectable by inhibition ELISA.

2. The method according to claim 1, wherein the amount of said antigen on the cell surface corresponds to at least 0.6 µg CS6/$10^9$ cells.

3. The method according to claim 1, wherein the amount of said antigen on the cell surface is at least 200% greater than an untreated cell and corresponds to at least 1.2 µg CS6/$10^9$ cells.

4. The method according to claim 3, wherein the amount of said antigen on the cell surface is at least 300% greater than an untreated cell and corresponds to at least 1.8 µg CS6/$10^9$ cells.

5. The method according to claim 1, wherein the selected duration of contacting time is from 1.5 to 42 h.

6. The method according to claim 1, wherein the selected temperature during the contacting time is from 18 to 42° C.

7. The method according to claim 6, wherein the selected temperature during the contacting time is from 18 to 38° C.

8. The method according to claim 7, wherein the selected temperature during the contacting time is from 18 to 22° C.

9. The method according to claim 7, wherein the selected temperature during the contacting time is from 36 to 38° C.

10. The method according to claim 1, wherein the cell is contacted with an aqueous solution comprising concentration of 0.8-2.0 percent phenol by weight.

11. The method according to claim 10, wherein the cell is contacted with an aqueous solution comprising concentration of 1.0-2.0 percent phenol by weight.

12. The method according to claim 1, wherein the cell is contacted with a phenol concentration of 0.6-2.0 percent by weight, for a time of 6-72 h and at temperature of 18-22° C.

13. The method according to claim 1, wherein the phenol concentration of the aqueous solution is 0.75-0.85 percent by weight, the duration of contacting time is 40±2 h and the temperature during the contacting time is 20±1° C.

14. The method according to claim 1, wherein the CS6 antigen is recombinantly overexpressed by the cell.

15. The method according to claim 1, wherein the cell after contacting is a killed whole cell.

16. The method according to claim 1, wherein the contacted cell is an *Escherichia coli* cell.

17. The method according to claim 1, wherein the method comprises contacting several cells concomitantly.

18. The method according to claim 17, further comprising comparing the presentation of the antigen by the cells to the presentation of CS6-antigen by untreated but otherwise comparable cells by an inhibition ELISA or dot blot.

19. The method according to claim 18, wherein the comparison is made by an inhibition ELISA.

20. The method of claim 17, wherein the phenol concentration, the temperature during the contacting time and the duration of contacting time are selected such that at least $10^7$-fold inactivation of the cells occurs concomitantly with the increase in CS6 antigen presentation.

21. The method according to claim 1, wherein the cell is contacted at a temperature of 20±1° C. with:
   about 0.6% phenol by weight for a duration of about 40 hours;
   about 0.8% phenol by weight for a duration of about 16 hours;
   about 0.8% phenol by weight for a duration of about 40 hours;
   about 1.0% phenol by weight for a duration of about 6 hours;
   about 1.0% phenol by weight for a duration of about 16 hours;
   about 1.0% phenol by weight for a duration of about 40 hours;
   about 1.2% phenol by weight for a duration of about 6 hours;
   about 1.2% phenol by weight for a duration of about 16 hours;
   about 1.2% phenol by weight for a duration of about 40 hours;
   about 1.5% phenol by weight for a duration of about 6 hours;
   about 1.5% phenol by weight for a duration of about 16 hours;
   about 1.5% phenol by weight for a duration of about 40 hours;
   about 2.0% phenol by weight for a duration of about 6 hours; or
   about 2.0% phenol by weight for a duration of about 16 hours.

22. The method according to claim 21, wherein the cell was treated with 1.0 to 1.5% phenol by weight for a duration of 6 to 40 hours at a temperature of 20±1° C.

* * * * *

SEQUENCE LISTING

```
<160> NUMBER OF SEQ ID NOS: 4

<210> SEQ ID NO 1
<211> LENGTH: 33
<212> TYPE: DNA
<213> ORGANISM: Artificial
<220> FEATURE:
<223> OTHER INFORMATION: Artificial primer

<400> SEQUENCE: 1
cggtctccct aggcctcctt acctatggtg atc                                    33

<210> SEQ ID NO 2
<211> LENGTH: 31
<212> TYPE: DNA
<213> ORGANISM: Artificial
<220> FEATURE:
<223> OTHER INFORMATION: Artificial primer

<400> SEQUENCE: 2
cggtctcctc gagcgactct agacctaacc g                                      31

<210> SEQ ID NO 3
<211> LENGTH: 41
<212> TYPE: DNA
<213> ORGANISM: Artificial
<220> FEATURE:
<223> OTHER INFORMATION: Artificial primer

<400> SEQUENCE: 3
cggtctcgaa ttctaatggt gttatatgaa gaaaacaatt g                           41

<210> SEQ ID NO 4
<211> LENGTH: 45
<212> TYPE: DNA
<213> ORGANISM: Artificial
<220> FEATURE:
<223> OTHER INFORMATION: Artificial primer

<400> SEQUENCE: 4
cggtctcaag cttaacattg tttatttaca acagataatt gtttg                       45
```